United States Patent
Buchan

(10) Patent No.: US 6,327,507 B1
(45) Date of Patent: Dec. 4, 2001

(54) MULTIPLE EXTENDABLE LEADWIRE DEVICE

(76) Inventor: Glenn M. Buchan, 660 Rambling Dr. Cir., Wellington, FL (US) 33414

(*) Notice: Subject to any disclaimer, the term of this patent is extended or adjusted under 35 U.S.C. 154(b) by 0 days.

(21) Appl. No.: 09/583,643

(22) Filed: May 30, 2000

Related U.S. Application Data

(63) Continuation-in-part of application No. 09/290,417, filed on Apr. 13, 1999, now abandoned.

(51) Int. Cl.$^7$ .................................................... A61N 1/00
(52) U.S. Cl. ........................................ 607/115; 191/12.4
(58) Field of Search ................................. 607/115, 148; 606/41; 191/12.4, 12.2 R, 12.2 A

(56) References Cited

U.S. PATENT DOCUMENTS

| | | |
|---|---|---|
| 3,964,490 | 6/1976 | Nelms . |
| 5,481,607 * | 1/1996 | Hsiao . |
| 5,535,960 | 7/1996 | Skowronski et al. . |
| 5,544,836 * | 8/1996 | Pera . |
| 5,590,749 | 1/1997 | Wagner et al. . |
| 5,690,198 * | 11/1997 | Lohr . |
| 5,701,981 | 12/1997 | Marshall et al. . |
| 5,796,047 * | 8/1998 | Sheng-Hsin . |
| 5,816,733 * | 10/1998 | Ishikawa et al. . |
| 6,045,393 * | 4/2000 | Alpert . |
| 6,056,591 * | 5/2000 | Liao . |
| 6,059,081 * | 5/2000 | Patterson et al. . |
| 6,059,213 * | 5/2000 | Phillips . |
| 6,199,674 * | 3/2001 | Liao . |

* cited by examiner

Primary Examiner—Mark Bockelman
(74) Attorney, Agent, or Firm—McHale & Slavin

(57) ABSTRACT

The present invention is directed toward a housing or magazine which is designed for efficient storage and management of electrically conductive cabling useful for the interconnection of disparate components, for example audio components, computer system components and the like. In a particular embodiment, the invention is directed toward a retractable lead wire device useful in the connection of patients to various input and output functions of medical testing and treatment devices, for example electrotherapy machines, ultrasound machinery, electrocardiogram machines (EKG) electroencephalograph (EEG) and devices useful for delivering muscle and nerve stimulation to the body. In a particular embodiment the device complies with the current IEC safety standards.

10 Claims, 3 Drawing Sheets

MULTIPLE EXTENDABLE LEADWIRE DEVICE

REFERENCE TO RELATED APPLICATIONS

This application is a continuation-in-part of Ser. No. 09/290,417, filed Apr. 13, 1999 and entitled "Retractable Lead Wire Apparatus for Electrotherapy Device" now abandoned, the contents of which are herein incorporated by reference.

FIELD OF THE INVENTION

This invention relates to lead wires for various types of electrical devices, particularly to a device for management of multiple lead wire devices useful in conjunction with electrotherapy apparatus, and most particularly to a retractable lead wire device for electrotherapy environments the construction of which is in compliance with IEC (International Electrotechnical Commission) Collateral Standard 601-1, Section 10, paragraph 56.3.

BACKGROUND OF THE INVENTION

Various systems are formed from a plurality of individual components which are interconnected by electrically conductive cabling. Illustrative of such systems are electrotherapy devices, computer systems, stereo systems and the like. A problem common to all such systems is the storage of the various connecting cables or lead wires necessary to interconnect the components. Excessive lengths of jumbled cables are unsightly as well as dangerous. A user or casual bystander might easily become entangled and subsequently injured due to excessive cabling. Furthermore, the cabling can represent a safety hazard, e.g. a fire might accidentally start due to a frayed cable or the user might suffer an electrical shock. Lastly, the excess cable is subject to wear and unnecessary abrasion which will cause it to become worn prematurely. Managing the number of wires required in complex systems becomes problematic, and the various lengths of the wires make it difficult, if not impossible to route them in a neat, organized and safe manner.

What is lacking in the art is an effective device for managing lead wires which utilizes a spring motor which is capable of maintaining a safe degree of tension on the wiring during its entire range of deployment. Additionally, the prior art lacks a wire management device that employs a braking mechanism which automatically maintains the wiring at a desired extension and subsequently enables easy and controlled retrieval, without damaging the wiring or connectors attached thereto.

DESCRIPTION OF THE PRIOR ART

U.S. Pat. No. 5,701,981 teaches a retractable and extendable electrical power cord, positionable within a wall. The reels utilize a spring which transfers an ever increasing tension to the cord as it is withdrawn. A locking mechanism or brake is further provided for stopping the reel when a desired amount of cord has been retracted. A particular deficiency inherent in this design is that the brake must be specifically engaged in order to fix the cord in place. Furthermore, the increasing tightness of the spring makes withdrawal more difficult as cord is withdrawn and creates a situation where the spring may retract the cord too forcefully when the brake is released. Lastly, the cable itself is likely to be damaged due to the excessive force necessary for movement.

U.S. Pat. No. 5,535,960 is drawn to a cord reel assembly which has a fixed cord and a retractable/extendable cord. The assembly is designed to eliminate sliding brushes and is designed to provide a constant connection without noise or interference. The mechanism utilizes a flat stationary cord having an even number of conductors, e.g. an eight conductor cable where 4 of the 8 conductors are used for signal transmission and the remaining 4 carry similar signals in opposite directions. The tension on the wire continually increases as the wire is extended and release of the pawl and ratchet results in a high speed retrieval which can be damaging to fragile wiring and connectors.

U.S. Pat. No. 5,590,749 is drawn to an electrical cord retraction device having a spiral wound flat conducting cable which can be wound about a mandrel and heat-treated to retain its tightly wound shape. In alternative embodiments, swiveling electrical contacts may be utilized to maintain electrical contact and a spring motor is tightened during extension to provide a force for retraction. The device does not provide a way of maintaining the cable in an extended position without a restraining force being applied by the user. Furthermore, the device is limited in that the wire remains under constant tension and must be of a sufficient strength to remain intact during numerous push/pull cycles.

U.S. Pat. No. 3,964,490 relates to a lead storage apparatus for electromedical devices. The patent discloses a device which is internally incorporated within a transcutaneous electrical nerve stimulating (TENS) unit. The device is formed integral with the TENS unit and has no independent utility. The device contains lead wires for the TENS unit in conjunction with a spring motor for developing tension during extension and a spring loaded braking device having an orifice through which the lead travels. Braking is accomplished by bringing pressure to bear upon the insulated lead wire. In a preferred embodiment, two leads are provided in such a manner that they rotate in opposite directions during extension and retraction thereby tensioning or relaxing the spring motor. The electrical contact is maintained via electrically conductive plates which are in contact with the lead wires and in turn with electrical brush contacts which electrically communicate with the TENS device. This device suffers from the fact that the leads are under constantly increasing tension and the braking is accomplished by placing a frictional and deforming force upon the wire and insulative covering. This will lead to premature failure of both the internal wiring and the insulative covering.

SUMMARY OF THE INVENTION

The present invention is directed toward a housing or magazine which is designed for efficient storage and management of electrically conductive cabling useful for the interconnection of disparate components, for example audio components, computer system components and the like. In a particular embodiment, the invention is directed toward a retractable lead wire device useful in the connection of patients to various input and output functions of medical testing and treatment devices, for example electrotherapy machines, ultrasound machinery, electrocardiogram machines (EKG) electroencephalograph (EEG) and devices useful for delivering muscle and nerve stimulation to the body. The device may be attached directly to the machine via a modular plug design thereby providing a compact and attractive storage area for lead wires. In a particular embodiment, the modular plug design prevents inadvertent connection to a mains power source and is in compliance with the current IEC safety standards. The device of the instant invention provides a portable lead wire which is independent of the electrotherapy unit or the like apparatus. The unique design provides for unimpeded withdrawal of the lead wire while simultaneously providing automatic braking to prevent unintended retraction, without applying any deforming force to the cable or its insulative jacket. In this manner, one or more of the lead wires may be used at variable lengths providing safe, convenient and reliable interconnection of multiple devices. While in transit or not in use, the outer housing provides a protective covering for the cabling. Furthermore, due to the novel spring design, the cables are not subjected to unduly high levels of tension which might cause stretching, delamination of the insulative jacket or breaking or fraying of strands of the conductor.

Accordingly, it is an objective of the instant invention to provide a housing for retractably storing electrical connecting cables in a safe and effective manner.

It is a further objective of the instant invention to teach a retractable lead wire device for electrotherapy machines.

It is an additional objective of the instant invention to teach a retractable lead wire device which employs an automatic braking system to prevent unintended recoiling.

It is yet another objective of the instant invention provide a device for protecting lead wires when not in use or during transport.

It is still another objective of the instant invention to provide a cable management device which includes an improved preloaded spring motor which acts to provide uniform and relatively constant tension to the electrically conductive cable during the full extent of its travel.

It is a still further objective of the invention teach a multiple lead wire management system which provides for independent usage of the lead wires and further enables combination therapy modalities.

Other objects and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

DETAILED DESCRIPTION OF THE INVENTION

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification and drawings.

It is further understood that while the device of the instant invention can be modified to manage a single electrically conductive cable or any number of cables, the following description will particularly illustrate an embodiment of the device including two cables.

Figure 1:
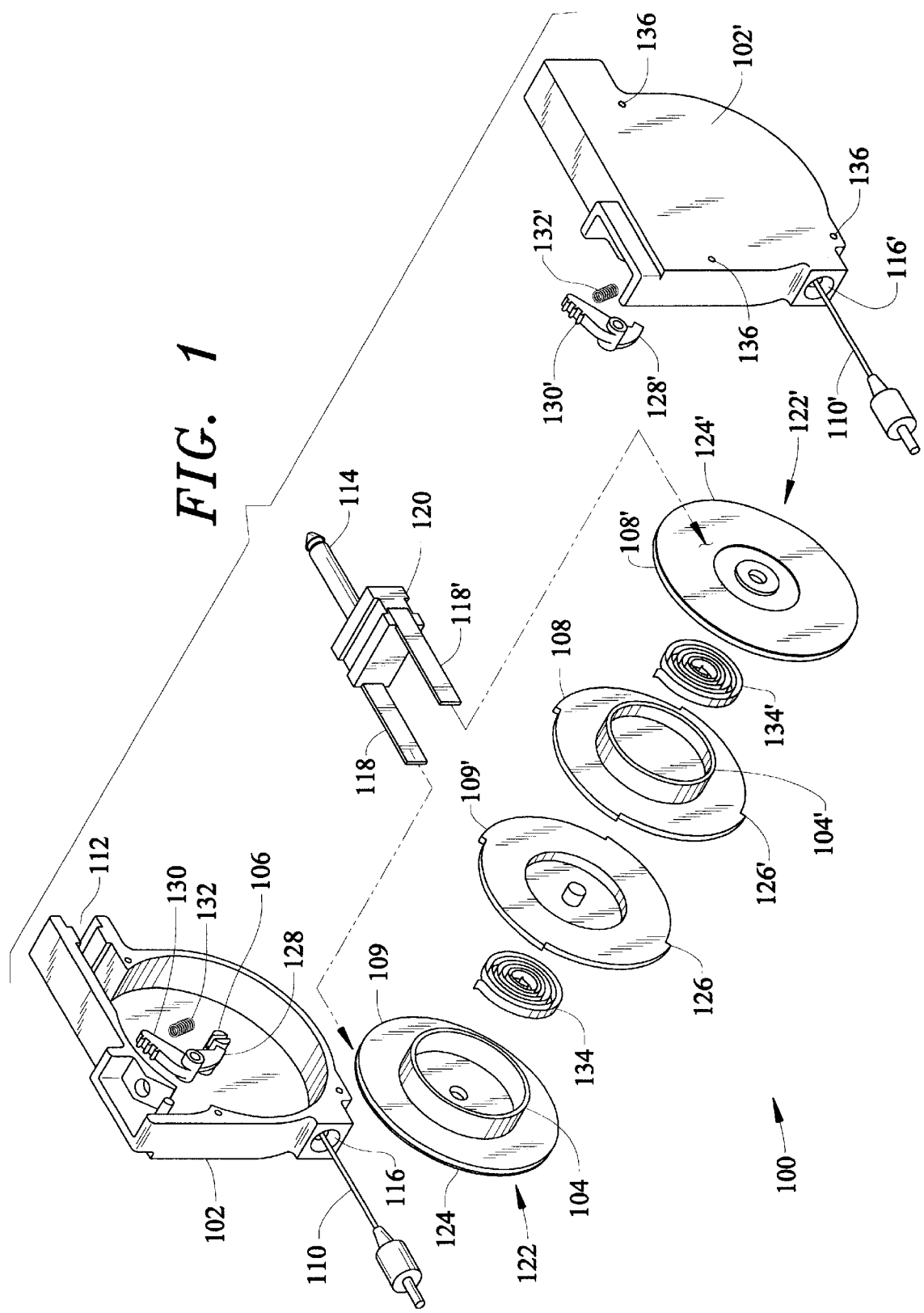
FIG. 1 is an exploded view of the device configured for managing two lead wires.

Now with reference to FIG. 1, the retractable cable management device 100 includes a two-part outer housing construction 102, 102' which is joined along a center line to form a unitary housing outer structure. As noted previously, although the particular embodiment illustrated is directed toward a two-conductor assembly, it is within the purview of the instant invention to utilize a single conductor embodiment. Upon assembly, the housing encloses at least one storage hub assembly 104, 104' which is journaled within said housing structure and positioned in coaxial alignment with the central axis defined by positioning posts or axles 106 and 106' (not shown) of the housing. The storage hub assembly is rotatable about said axis defined by the positioning posts. Pairs of essentially circular flanges 108,108' and 109,109', which are axially spaced-apart, extend from and are essentially perpendicular to the axis of the storage hub assembly, to define cable storage areas therebetween. When in its storage mode, the cable 110,110' remains wound about the storage hub assembly. The housing further includes a first opening 112 adapted to receive a coupling device 114, for example a dual conductor phone plug. The housing also includes a point of ingress/egress 116,116' for each electrically conductive cable. Each conductor 118,118' of the dual conductor plug is in electrical communication, via a junction box 120, with a contact plate 122,122', which in a preferred embodiment is a beryllium copper contact plate. In a particularly preferred embodiment, each said contact plate 122,122' includes an annular region 124,124' which is coated, e.g. with a beryllium or alloy thereof, to define a conductive area upon one of said essentially circular flanges, to which area the electrically conductive cable has been connected, thereby providing electrical continuity. The other of said flanges includes radially spaced-apart detents or notches 126,126' at the peripheral edges thereof. These detents are constructed and arranged to allow the cable to be extracted freely when the storage hub assembly is rotated in a first direction, however the detents engage the tab 128,128' of a biased braking ratchet mechanism 130,130' when rotated in the opposite direction. As illustrated, the mechanism is biased to engage the detents via the force exerted by spring 132,132'. In the instant embodiment, the cables 110,110' may be extracted from the device independently or in tandem. In order to insure smooth operation of the device, torsion springs 134,134' are positioned between the housing and the adjacent flange. The torsion springs are in mechanical engagement with both the housing 102,102', by virtue of mechanical engagement with slots in positioning posts 106, 106' and by mechanical anchoring to storage hub assembly 104,104', and are initially biased so as to maintain a slight retracting force when in the fully retracted position, which force may increase slightly as the cable is extended for use. In a particularly preferred embodiment, the spring biasing means may comprise an extended eye spring assembly. This spring assembly represents an improvement over conventional backwound springs because it actually increases available torque with fewer initial turns or prewinds. In the extended eye design, prewinds are formed by alternating layers of the eye and spring element. This results in a more economical spring design and improved performance due to the torque increase in the initial few turns producing a flatter torque curve over the entire working range of the spring. Thus, a relatively constant tension is applied to the cable while it is being extended and retracted from the housing which results in more reliable and efficient operation, and is much less injurious to the cable and its insulative outer covering.

Figure 2:
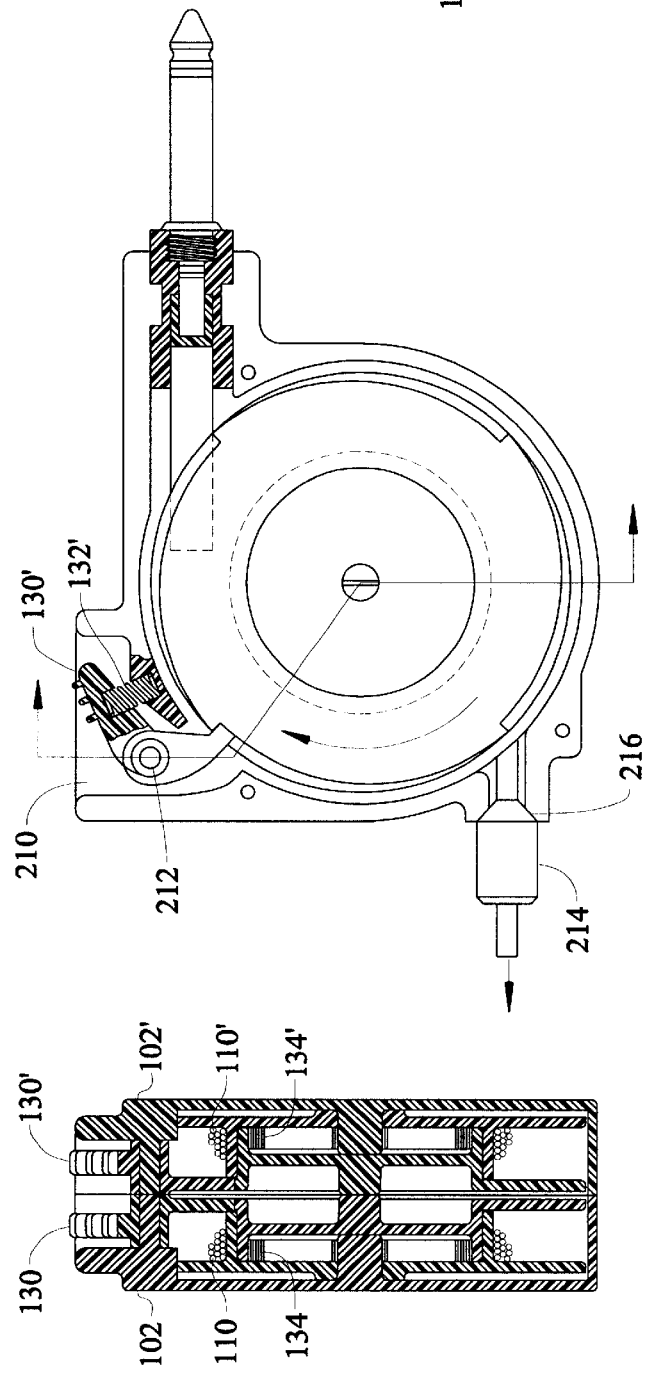
FIG. 2 is a cross-sectional view of the device.

Referring now to FIG. 2, a cross-sectional view displaying one of the two brake/release levers or ratchets 130' is shown. The levers are positioned within the housing 102, 102' in a safety area 210 to protect against premature activation. Each lever pivots about a positioning axle 212 which is molded into the outer housing. A small compression spring 132' applies sufficient force to the lever to engage one of the cam detents, thereby preventing the wire from retracting until desired. In use, the levers ride up the cam surface as the cable is withdrawn, ratcheting over the locking detents located peripherally on the outer flange, and returning the cable to the closest locking position, at maximum one quarter revolution. The cable may end in a typical molded connection 214, as herein depicted, which is attachable to an electrode patch worn by a patient (not shown) or the like sensor or contact. The area adjacent the opening through which the wires pass from the housing 216 can be molded to accept the molded connection and retain it in a particular orientation.

Figure 3:
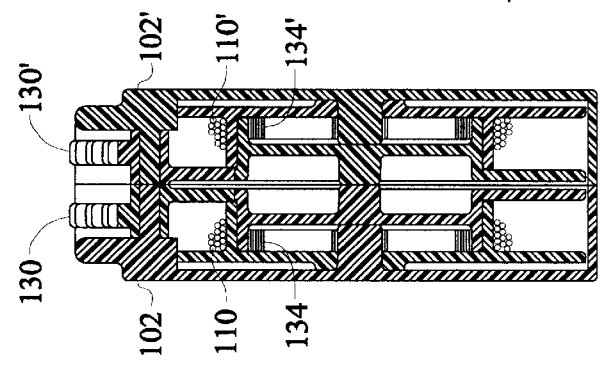
FIG. 3 is a cross-sectional view taken through line 3—3 of FIG. 2.

As best seen in FIG. 3, spirally wound spring motors 134,134' operate independently to apply sufficient retractive force for rewinding the wires to a storage position. Since the operation of each motor is totally independent, the wires 110,110' can be extracted to varying lengths during use and rewound independently. A thrust bearing (not shown), may be located between the innermost flanges, to separate the distinct storage assemblies, thereby creating an area of clearance to allow for independent operation with reduced friction.

Figure 4:
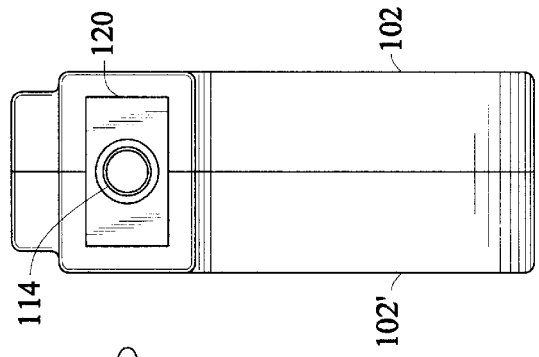
FIG. 4 is an end view of the device.

Referring to FIG. 4, an end view of the device is shown including a left side housing 102' and a right side housing 102. The sides are positioned together with all internal components secured therein and are fixedly engaged by an attachment member or members (not shown), e.g. screws positioned at apertures 136 (see FIG. 1) positioned along the central axis. An electrical attachment plug 114, for example a modified ¼" commercial phone plug having flexible plus and minus insulated connectors (not shown) are embedded within a molded junction box 120.

Figure 5:
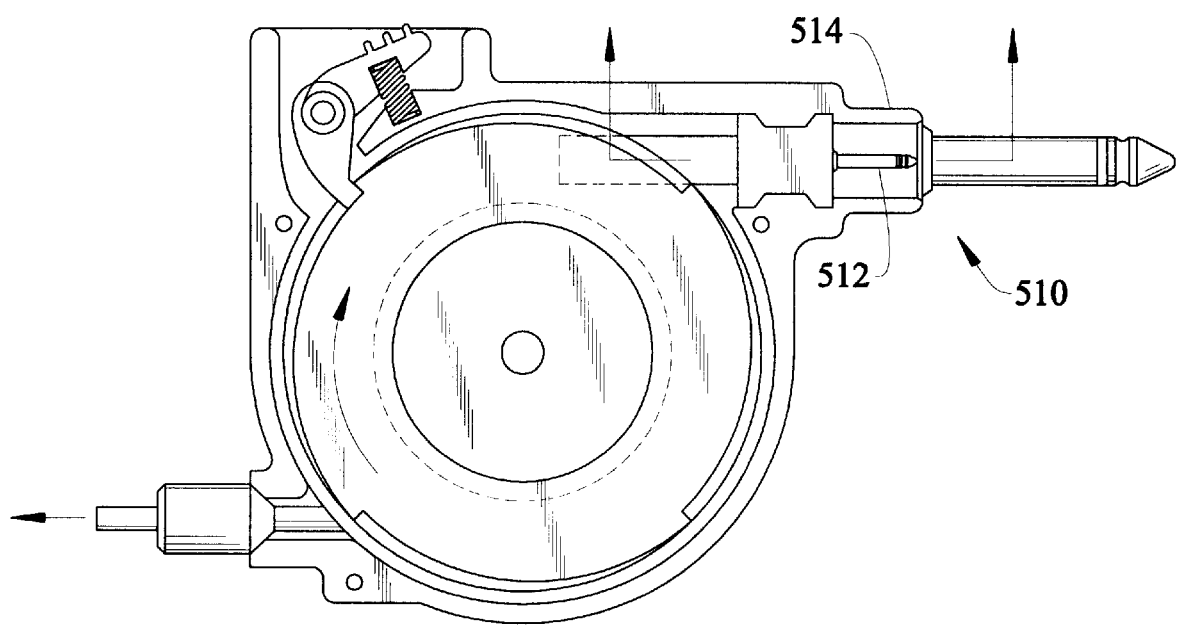
FIG. 5 is a cross-sectional view showing an embodiment containing a patient protective conductive connection.

With reference to the embodiment illustrated in FIG. 5, an alternative attachment plug assembly 510 is shown wherein a smaller male plug 512 is recessed within an extended shoulder 514 which is integral with the two-part outer housing construction 102,102. In this manner, the structure is in compliance with IEC Collateral Standard 601-1, Section 10, paragraph 56.3. A second larger connector 516 having a male and female end, overlies the internally located connector and provides electrical connection with the desired device.

Figure 6:
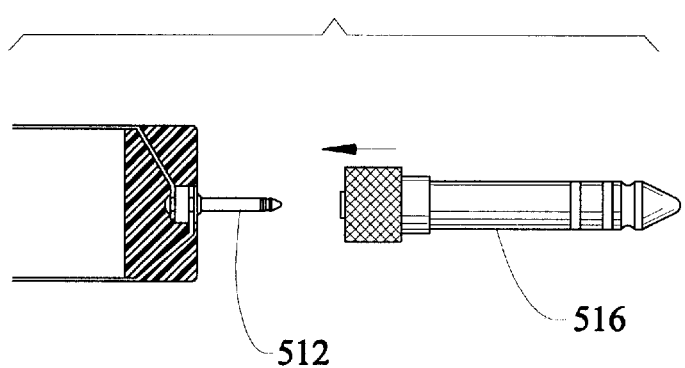
FIG. 6 is an exploded view of the patient protective modular plug assembly.

FIG. 6 represents an exploded view of plugs 512 and 516 which come together to form a patient protective modular plug assembly.

What is claimed is:

1. A device for management and storage of at least a first and a second electrically conductive cable useful for interconnecting plural components comprising: a housing outer structure including means for ingress/egress of said electrically conductive cables;
    at least a first and second cable storage means constructed and arranged for independent rotation with respect to each other mounted within said housing; said housing means including an electrical coupling means thereon effective for conducting a first and second component of a signal from an external device;
    at least first and second conductor means for electrically connecting said electrical coupling means to said at least first and second cable storage means and to at least a first and second cable member such that a first signal component is delivered only to said first storage means and said first cable member and a second signal component is delivered only to said second storage means and said second cable member;
    retraction means in mechanical engagement with said housing outer structure and said cable storage means for retracting said cables to a fully stored position.
2. The device in accordance with claim 1, wherein:
    said housing outer structure has a first half and a second half.
3. The device in accordance with claim 1, wherein:
    said at least first and second means for cable storage rotatably mounted within said housing includes at least a first and second storage drum assembly rotatably mounted within said housing and including an axle, a first essentially circular flange and a second essentially circular flange, each said flange arranged in spaced-apart relation along said axle and essentially perpendicular thereto, thereby defining a cable storage area adapted to releasably store an electrically conductive cable therein.
4. The device in accordance with claim 3, wherein:
    said conductor means include an electrically conductive annular region located on said first flange and in electrical communication with said electrically conductive cable.
5. The device in accordance with claim 1, wherein:
    said coupling means include a supply plug integrally engaged with said housing outer structure and in electrical communication with an electrically conductive surface.
6. The device in accordance with claim 1, wherein:
    said retraction means includes at least one spring motor.
7. The device in accordance with claim 1, including:
    cable transport control means in frictional engagement with said cable storage means for automatically preventing retraction.
8. The device in accordance with claim 1, wherein:
    said coupling means includes a two-part plug assembly wherein a first part of said plug assembly is recessed within a cavity of said outer housing and is adapted for electrically coupling to a second part of said plug assembly.
9. The device in accordance with claim 7, wherein said cable transport control means in frictional engagement with said cable storage means for automatically preventing retraction includes:
    at least one brake/release lever positioned within said unitary housing outer structure, said lever constructed and arranged to pivot about an axle which is molded into said unitary housing outer structure and is spring biased for application of a force sufficient to frictionally engage said cable storage means.
10. The device in accordance claim 1, wherein the first and second cable storage means include a first and second cable stored thereon in the form of a first and second medical lead.

* * * * *